(12) United States Patent
Post et al.

(10) Patent No.: US 8,161,974 B2
(45) Date of Patent: Apr. 24, 2012

(54) HEARING PROTECTION APPARATUS WITH INCORPORATED EYEWEAR

(75) Inventors: Gregory D. Post, Fairport, NY (US); Jozef J. Zwislocki, Fayetteville, NY (US); Robert J. DiNardo, Webster, NY (US)

(73) Assignee: Syracuse University, Syracuse, NY (US)

( * ) Notice: Subject to any disclaimer, the term of this patent is extended or adjusted under 35 U.S.C. 154(b) by 254 days.

(21) Appl. No.: 12/542,993

(22) Filed: Aug. 18, 2009

(65) Prior Publication Data

US 2010/0065069 A1 Mar. 18, 2010

Related U.S. Application Data

(60) Provisional application No. 61/089,963, filed on Aug. 19, 2008.

(51) Int. Cl.
| | |
|---|---|
| *A61F 11/00* | (2006.01) |
| *A61F 11/06* | (2006.01) |
| *H04R 25/00* | (2006.01) |
| *A61B 7/02* | (2006.01) |
| *G02C 1/00* | (2006.01) |

(52) U.S. Cl. ........ 128/866; 128/867; 181/129; 181/135; 351/158

(58) Field of Classification Search .................. 128/866, 128/864, 867; 181/130, 131, 129, 135; 2/209, 2/423–424, 426–431, 439–448, 11, 13, 15; 351/158

See application file for complete search history.

(56) References Cited

U.S. PATENT DOCUMENTS

| | | | |
|---|---|---|---|
| 2,545,731 | A | 3/1951 | French |
| 3,565,069 | A | 2/1971 | Miller |
| 3,690,404 | A | 9/1972 | Collins |
| 3,851,123 | A | 11/1974 | Lipinski et al. |
| 3,863,028 | A | 1/1975 | Fixler |
| 3,939,310 | A | 2/1976 | Hodges |
| 4,006,796 | A | 2/1977 | Coehorst |
| 4,110,583 | A | 8/1978 | Lepper |
| 4,173,715 | A | 11/1979 | Gosman |
| 4,387,784 | A | 6/1983 | Hill |
| 4,418,787 | A | 12/1983 | Eggert et al. |

(Continued)

OTHER PUBLICATIONS

"Helmholtz Resonator—DiracDelta Science & Engineering Encyclopedia", http://diracdelta.co.uk/science/source/h/e/helmholtz%20resonator/source.html, Jan. 13, 2008, pp. 1-2.

(Continued)

*Primary Examiner* — Patricia Bianco
*Assistant Examiner* — Ophelia Hawthorne
(74) *Attorney, Agent, or Firm* — Hiscock & Barclay, LLP

(57) ABSTRACT

An apparatus for providing hearing protection to a wearer includes an incorporated set of eyewear having an eyewear frame. In one version, a pair of ear muffler tubes are coupled to the supporting members of the frame or made integral therewith, the muffler tubes each extending to the entrance of the ear canal of a person to reduce the level of ambient noise in the ear canal and includes at least one muffler tube of appropriate dimensions sufficient to isolate the ear canal from ambient air that substantially reduces the acoustic impedance at the entrance of the ear canal over a wide range of audible sound frequencies. A connecting tube for attachment to the ear canal is coupled to the ear muffler tube.

24 Claims, 7 Drawing Sheets

U.S. PATENT DOCUMENTS

| | | | |
|---|---|---|---|
| 4,424,880 A | | 1/1984 | Murayama et al. |
| 4,441,576 A | | 4/1984 | Allen |
| 4,571,746 A | | 2/1986 | Gorike |
| 4,807,612 A | | 2/1989 | Carlson |
| 4,852,683 A | | 8/1989 | Killion |
| 4,864,610 A | | 9/1989 | Stevens |
| 4,972,488 A | | 11/1990 | Weiss |
| 5,022,486 A | | 6/1991 | Miura et al. |
| 5,113,967 A | | 5/1992 | Killion et al. |
| 5,276,740 A | | 1/1994 | Inanaga et al. |
| 5,390,369 A | | 2/1995 | Tubin |
| 5,703,670 A | | 12/1997 | Callard |
| 5,718,002 A | | 2/1998 | Pavlak |
| 5,781,272 A | * | 7/1998 | Bright et al. .......... 351/123 |
| 5,824,967 A | * | 10/1998 | Zwislocki ............ 181/130 |
| 5,987,653 A | | 11/1999 | Cyr |
| 6,067,664 A | | 5/2000 | Cortes |
| 6,678,897 B2 | | 1/2004 | Lindgren |
| 6,758,304 B1 | | 7/2004 | McLean |

OTHER PUBLICATIONS

"Helmholtz Resonator", http://physics.kenyon.edu/EarlyApparatus/Rudolf_Koenig_Apparatus/Helmholtz_Resonat..., Jan. 13, 2008, pp. 1-3.

"Helmholtz Resonance", http://www.phys.unsw.edu.au/jw/Helmholtz.html, Jan. 13, 2008, pp. 1-4.

"Acoustic/Flow-induced Oscillations of a Helmholtz Resonator", http://en.wikibooks.org/wiki/Acoustics/Flow-induced_oscillations_of_a_Helmholtz_reason..., Jan. 13, 2008, pp. 1-7.

"Helmholtz Resonant Absorber", http://www.audioholics.com/education/acoustics-principles/helmholtz-resonant-absorber, Jan. 13, 2008, pp. 1-2.

"Helmholtz Resonant Absorber—p. 2", http://www.audioholics.com/education/acoustics-principles/helmholtz-resonant-absorber/h..., Jan. 13, 2008, pp. 1-3.

International Search Report for PCT/US2009/054142, mailed Mar. 24, 2010 (11 pages).

Supplementary European Search Report, dated Aug. 19, 2011 (5 pages).

* cited by examiner

HEARING PROTECTION APPARATUS WITH INCORPORATED EYEWEAR

CROSS REFERENCE TO RELATED APPLICATIONS

The following application claims priority to a provisional patent application U.S. Ser. No. 61/089,963, entitled Hearing Protection Apparatus With Incorporated Eyewear, filed Aug. 19, 2008, the entire contents of which are herein incorporated by reference.

FIELD OF THE INVENTION

The present invention generally relates to the field of hearing protection devices and more specifically relates to the incorporation and/or integration of eyewear within a passive hearing protection device.

BACKGROUND OF THE INVENTION

Presently, noise insulation or hearing protector devices are commonly known in the field. Such devices include either: i) ear muffs that cover the entire outer ear; ii) ear plugs that are inserted into the ear canal; or iii) semi-inserts that seal the ear canal at its entrance. Though each of these devices have their own advantages and disadvantages, a semi-insert version developed by Applicant provides acceptable noise protection over the audible frequency range. These latter devices also avoid the problems of earplugs in that they do not enter the ear canal and are cheaper and less cumbersome than ear muffs.

Presently, eye goggles or other protective eyewear are also commercially available to construction or industrial workers, laborers, and other individuals in order to provide wearers with suitable protection from particulates, chemicals, debris, and other materials. There are occasions, however, in which these and other individuals desire hearing protection in addition to eye protection when involved in work or other related activities. It would therefore be desirable as well as advantageous to provide an hearing protection apparatus that incorporates or otherwise includes a set of eyewear. Such an improvement would be viewed as a meaningful advance and a solution to existing problems that are presently confronted.

SUMMARY OF THE INVENTION

Therefore and according to one embodiment, an apparatus is provided for reducing ambient noise to the ear of a wearer including a hearing protection device that includes a set of eyewear incorporated therein. The hearing protection device according to a preferred embodiment is a passive semi-insert hearing protection device.

According to one version, the passive semi-insert hearing protection device comprises a pair of muffler tubes, each of said muffler tubes including an open end for coupling to the ear canal and a closed opposite end, said closed end being coupled to the eyewear frame, said tubes each having a sufficient length to provide a quarter wave sound resonance, said muffler tubes forming at least a portion of the eyewear frame.

The open end of each muffler tube forms a tight acoustic coupling to the ear canal with the help of a resilient sealing cuff and the closed end is attached to or integrated within the eyewear frame. Each muffler tube is defined by appropriate dimensions to have a substantially lower acoustic impedance at its open end than the acoustic impedance at the entrance of the ear canal over a wide range of audible sound frequencies. This low acoustic impedance can be achieved by making the inner cross sectional area of the tube substantially greater than the cross sectional area of the ear canal and/or by making the tube length equal to a quarter wavelength of sound at a desired frequency so as to produce a quarter wave resonance.

The open end of each of the muffler tubes should have an inner cross sectional area of at least, but preferably greater than approximately 1.15 $cm^2$, and a length greater than 4 cm to sufficiently reduce the acoustic impedance at the ear canal entrance and usefully increase the sound attenuation at the ear over a satisfactory frequency range. In one embodiment, the interior of each muffler tube is filled, at least partially, with a light sound-absorbing or damping material or other acoustic resistance element(s).

Each ear muffler tube can be shaped as needed to provide the needed noise reduction. In one version, each ear muffler tube is made, such as by blow molding, from a single unitary section that is adjustably attached to the remainder of the eyewear frame. In another version, the tubes can be manufactured from multiple interlocking sections or otherwise formed wherein each tube can be tapered or can be made with varying geometries in which sound-absorbing material or other acoustic resistance element(s) may not be required at the juncture of the connecting tubes. The ear muffler device design provides increased noise attenuation without increasing the necessary pressure on the soft tissues surrounding the entrance of the ear canal and without appreciably increasing the bulk and cost of the overall apparatus in terms of its weight or its manufacture so as not to interfere with the comfort of the wearer.

According to another version, the passive semi-insert hearing protection apparatus employs a Helmholtz-type resonator. This resonator can be formed by means of an enclosure that is sized substantially to that of the outer ear of the wearer, but having an interior air volume that is not smaller than about 7 cc. The enclosure is attached or formed within the frame of eyewear that can be worn by the user. The enclosure is defined by thin walls made from a rigid or semi-rigid material and a short tube extending from the enclosure that communicates with the ear canal, the short tube having a cuff which is larger than that of the average ear canal. The hearing protection apparatus according to this version has an acoustic impedance at a distal end of the short tube that is substantially smaller than the acoustic impedance at the entrance of the ear canal over a useful range of audible sound frequencies.

According to yet another aspect, the herein described hearing protection apparatus with incorporated eyewear, can be constructed for connection to a sound transmitting device, for example, an MP3 player, tape player, portable stereo, or other suitable device having speakers and/or a microphone. For example and according to this concept, earphones are attached within a closed end of each muffler tube. Alternatively, a sound transmitting device, including speakers and a microphone, can be integrated within the hearing protection (e.g., ear muffler) device itself.

One advantage realized is that a single apparatus can be equipped to provide both adequate hearing and eye protection, thereby providing a very useful and practical device for workers in various fields not limited to construction, aircraft, industrial, and others.

Another advantage of the herein described invention is that the hearing protection device design can easily be modified dimensionally and depending on the desired application to better customize the amount of noise reduction, particularly with regard to specific frequency levels.

These and other features and advantages will be described in greater detail in the following Detailed Description, which should be read in conjunction with the accompanying drawings.

DETAILED DESCRIPTION

The following description relates to various embodiments of apparatus for reducing the amount of ambient noise reaching the ear canal. More particularly, the description relates to the incorporation or integration of a specific form (i.e., safety goggles) of eyewear within this apparatus to provide enhanced protection. It will be appreciated that other suitable variations and/or modifications will be apparent to those of sufficient skill in the field. In addition and throughout the course of discussion various terms such as "top", "bottom", "above", "below", and the like are used in an effort to provide a suitable frame of reference for the accompanying drawings. To that end, these terms are not intended to be limiting of the inventive concepts described herein, except where so specifically indicated.

For purposes of the present discussion, "eyewear" refers to eyeglasses, sunglasses, goggles, protective glasses or sunglasses, prescription glasses and the like including lenses, frames, hinges, nose pieces and other related components. In addition, "hearing protection" apparatus and "noise reduction" apparatus or devices are referred to throughout synonymously and are intended to be equivalent terms.

Figure 1:
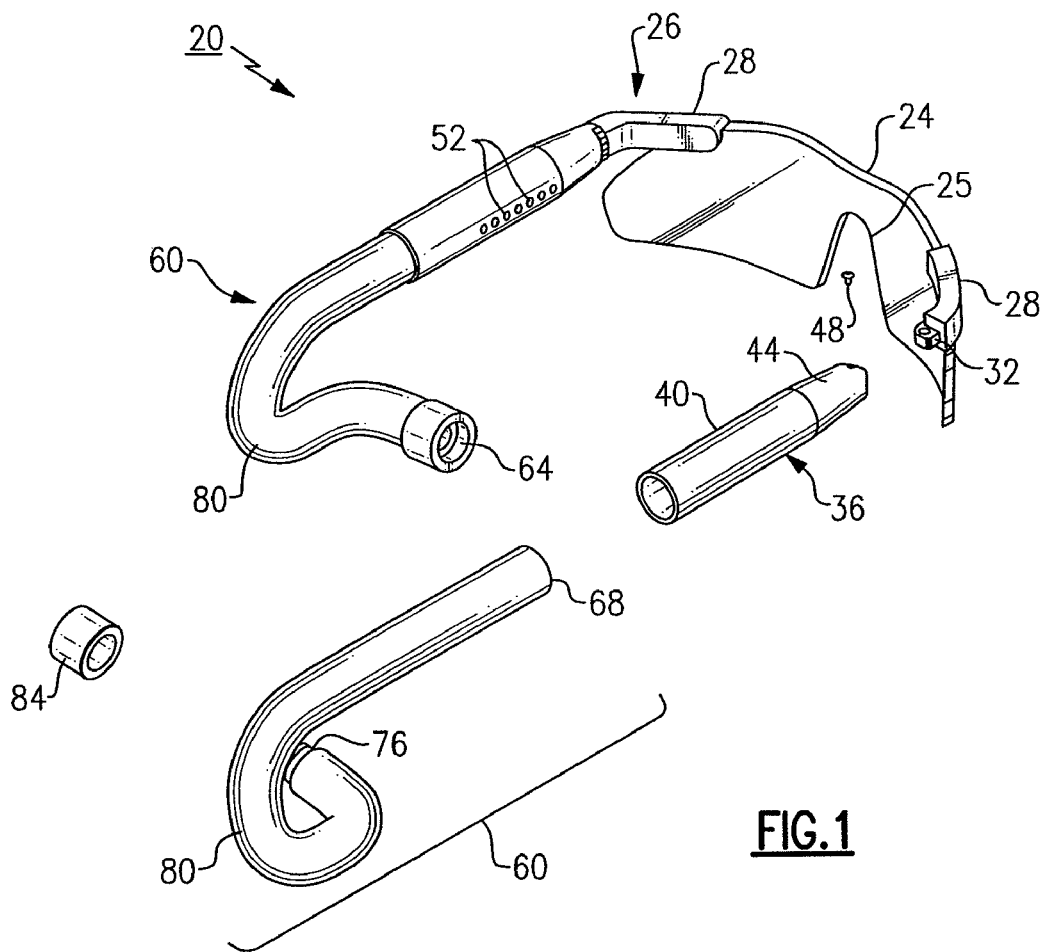
FIG. 1 is a partially exploded assembly view of a passive noise reduction device that has been configured to include eyewear in accordance with one embodiment of the present invention.
Figure 2:
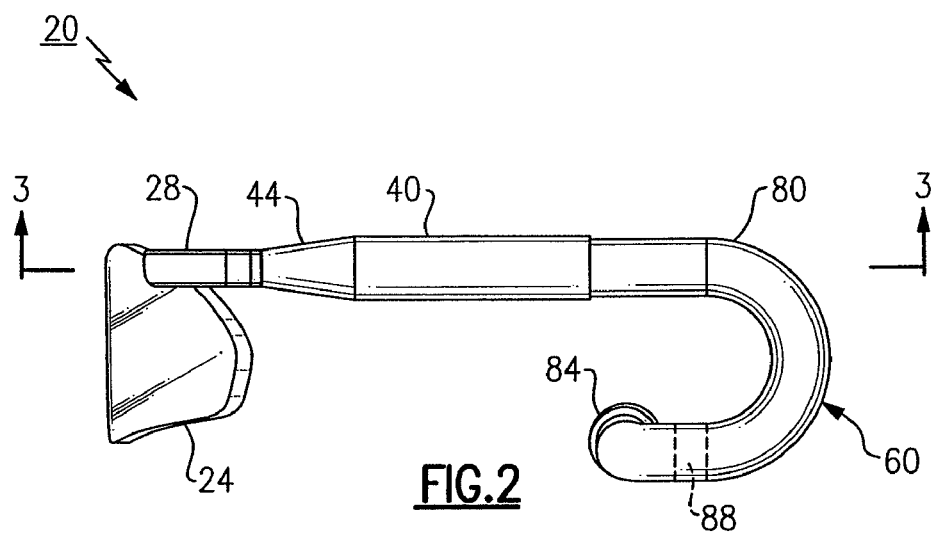
FIG. 2 is a side elevational view of the apparatus depicted in FIG. 1.
Figure 3:
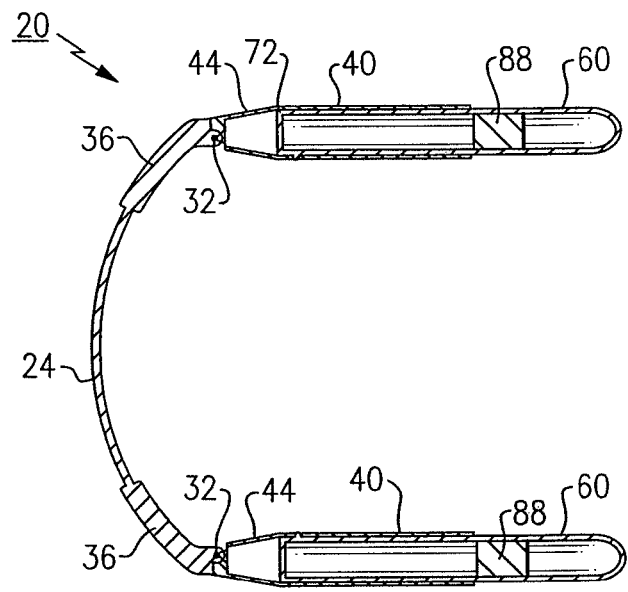
FIG. 3 is a sectioned view of the apparatus of FIGS. 1 and 2 taken through line 3-3 of FIG. 2.
Figure 4:
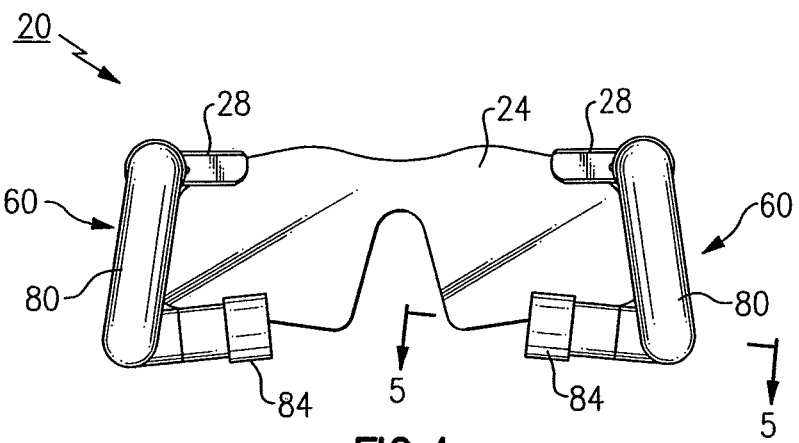
FIG. 4 is a rear facing view of the apparatus of FIGS. 1-3.
Figure 5:
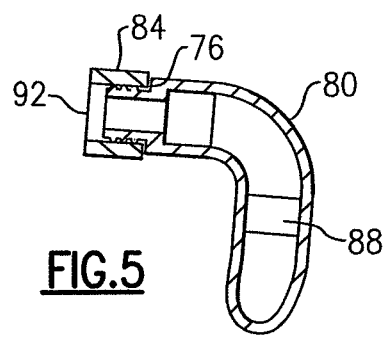
FIG. 5 is a sectioned view of an ear cuff of the apparatus as taken through line 5-5 of FIG. 4.
Figure 6:
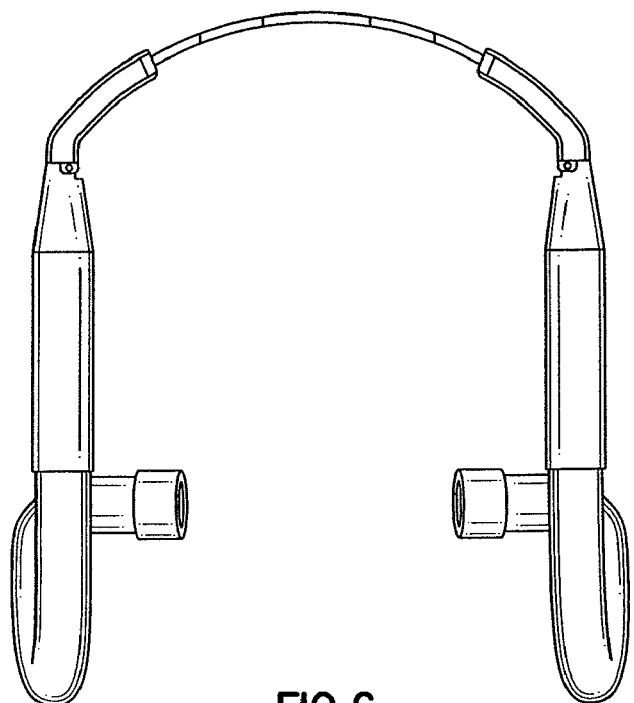
FIG. 6 is a top plan view of the apparatus of FIGS. 1-5.
Figure 7:
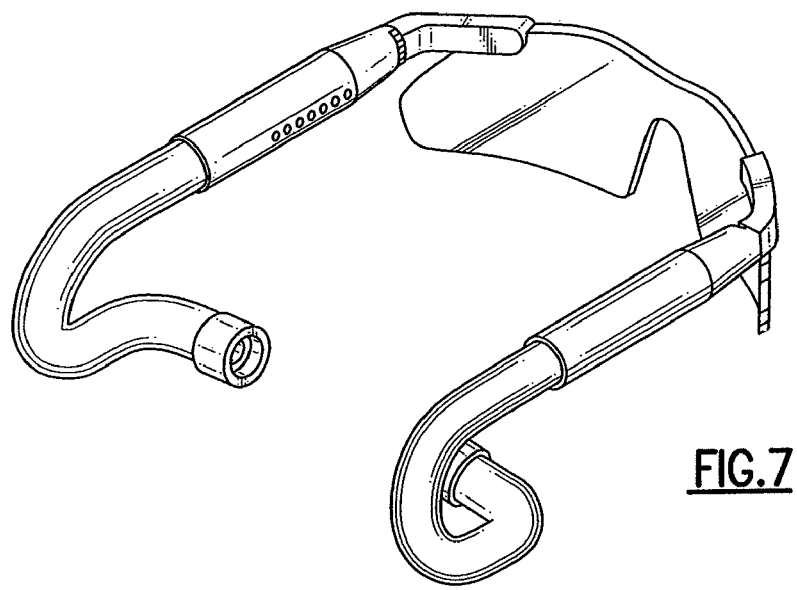
FIG. 7 is a side perspective view of the apparatus of FIGS. 1-6.
Figure 8:
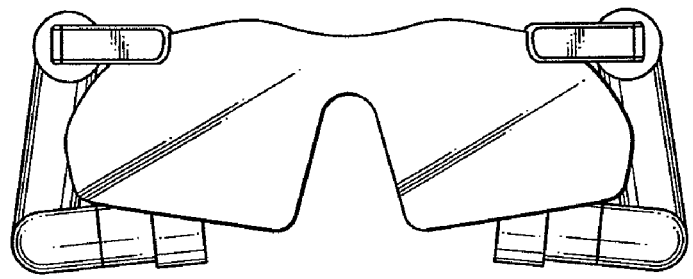
FIG. 8 is a front facing view of the apparatus of FIGS. 1-7.
Figure 9:
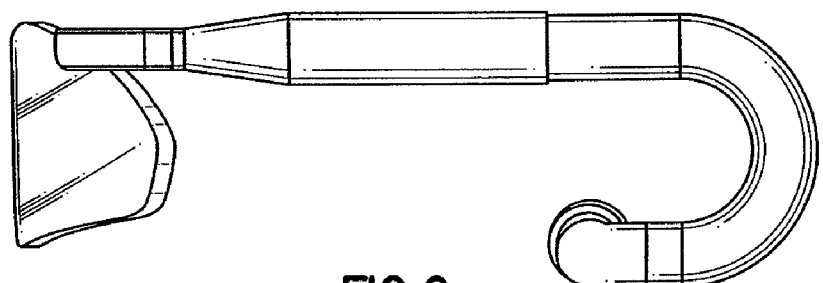
FIG. 9 is a right side facing view of the apparatus of FIGS. 1-8.
Figure 10:
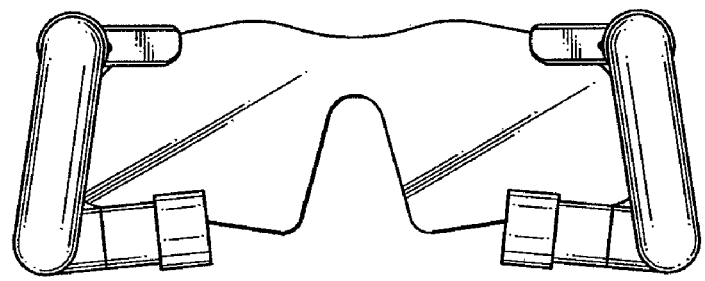
FIG. 10 is the rear facing view of the apparatus of FIG. 4, without the section line.
Figure 11:
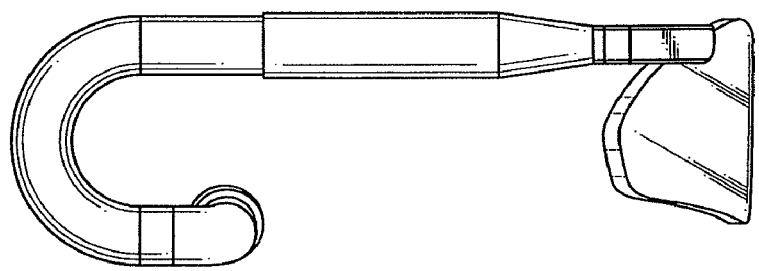
FIG. 11 is a left side facing side of the apparatus of FIGS. 1-10.
Figure 12:
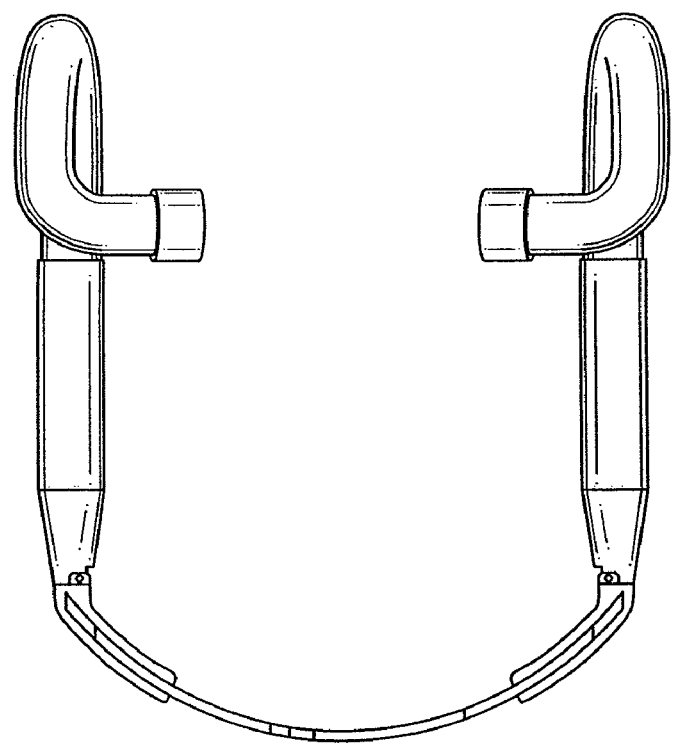
FIG. 12 is a bottom view of the apparatus of FIGS. 1-11.
Figure 13A:
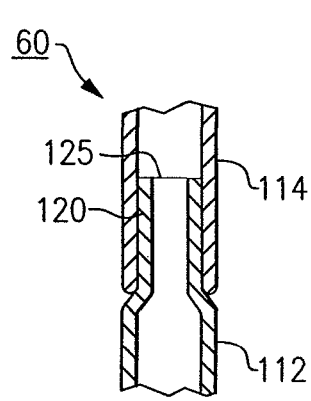
FIGS. 13(a)-(e) are sectional views of a portion of the apparatus of FIGS. 1-12, illustrating alternative versions of a connection technique between adjacent sections thereof.
Figure 13B:
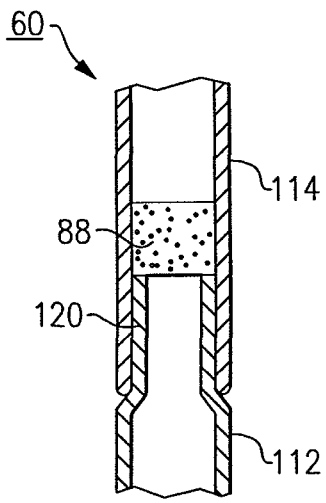
Figure 13C:
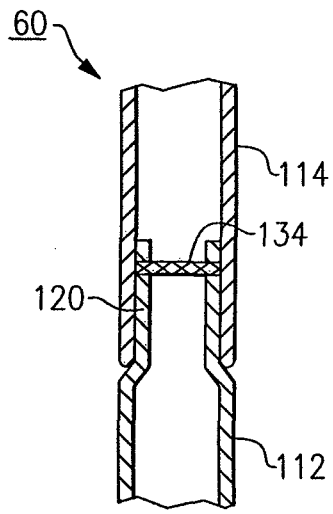
Figure 13D:
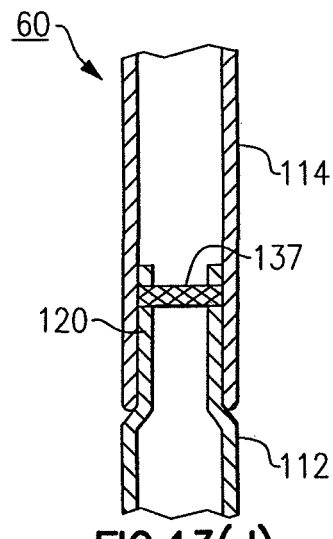
Figure 13E:
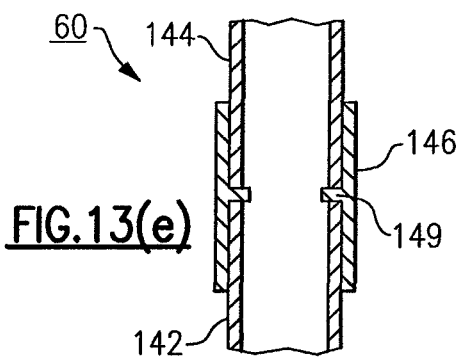

Referring to FIG. 1, a noise reduction apparatus 10 in accordance with an exemplary embodiment is depicted that includes a set of eyewear and more particularly, a set of safety goggles 20. A eye shield 24, made from a curved section of a durable lightweight transparent material, is retained by a frame 26 that includes a pair of hinge members 28. The eye shield 24 can be made optically clear or can be tinted. The hinge members 28 are each shaped to conform to the curvature of an end portion of the eye shield 24 and are disposed on opposite sides thereof. The eye shield 24 is retained within a slot (not shown) that is formed in the bottoms of each hinge member 28, with the shield spanning therebetween and beneath the hinge members. The eye shield 24 further includes a recess 25 formed in the lower portion at the center of the span thereof, this recess being configured to fit over the nose (not shown) of the wearer. Nose guards (not shown) can also be added for comfort. Alternative attachment means, including adhesives and fasteners, heat sealing or ultrasonic welding, could also be utilized to effectively secure the eye shield 24 to the hinge members 28. According to yet another alternative design, the eye shield 24 could be made integral with the eyewear frame 26 as a single component.

For purposes of the present invention, the herein described frame is intended to be exemplary as there are numerous forms of eyewear frames that are known, including those used for supporting separate lens elements, including lenses having optical power for magnification and/or for eye correction of the wearer. The concepts that are described herein are intended to cover these variations.

Referring to FIG. 1, an extending end of each hinge member 28 includes a hinge joint 32 (only one of which is shown in FIG. 1) that is secured to corresponding front support members 36 of the eyewear frame 26. Each of the front support members 36 include a hollow tubular section 40 extending into a distal attachment section 44, the latter being attached to the hinge joint 32 by means of a threaded fastener 48. Each of the hollow tubular sections 40 include a plurality of linearly spaced holes 52 extending axially from an intermediate section to a point that is adjacent the distal attachment section 44.

The eyewear of the present invention further includes a hearing protection device of the semi-insert type, the latter being equipped with a tube of appropriate dimensions for each ear, therefore, called the "muffler tube" or "ear muffler tube". More particularly, the herein described eyewear further comprises a pair of ear muffler tubes 60. Each muffler tube 60 is in air communication with the ear canal (not shown) and is tightly acoustically coupled thereto with the help of an appropriate sealing device as now described.

Referring to FIGS. 1-5, each ear muffler tube 60 is defined by an open end 64 and a closed end 68, the closed end being sized to be fitted within the interior of the hollow tubular section 40 of each of the front support members 36. One ear muffler tube 60 is shown as disassembled in FIG. 1 for purposes of clarity.

The ear muffler tubes herein described are passive semi-insert noise reduction devices, the principle of which is described in greater detail below. The tube 60 is connected to the ear canal at the opposite open end 64 by a connecting tube 76 having a reduced diameter for a better fit to the outer ear of the wearer. The end of the connecting tube 76 defines an opening 92, FIG. 5, to provide communication with the outer ear (not shown). A tight fit of the connecting tube 76 to the ear surface around the ear canal is achieved by means of the soft cuff 84 that is fastened to the exterior of the connecting tube 76, the cuff having an exterior dimension that is slightly larger than that of the outer ear (not shown). The remainder 80 of each muffler tube is defined by a curved configuration wherein interior of each muffler tube 60 is at least partially filled with light sound-absorbing or damping material 88 (shown in FIGS. 2 and 5), such as but not limited to open-cell foam rubber, cotton, felt or nylon fibers. Alternatively, other acoustic resistance elements can be used. To achieve a tight seal around the ear canal entrance, the front support members 36 preferably include a spring or other biasing means disposed within the distal attachment section 44 that causes the eyewear frame 26 to press inwardly against the head of the wearer, thereby gently pressing each connecting tube 76 against the ear, so as to compress each soft cuff 84 with the ear canal (not shown) and effectuating a proper seal.

The closed end 68 of the muffler tube 60, when fitted into the confines of the hollow tubular section 40 of the front support member 36 permits axial adjustment by means of a detent, tab or other means (not shown), extending from an outer surface that is aligned with the linear set of holes 52 to provide a series of adjustment positions.

The components of the ear muffler tubes 60 may be made of any suitable materials, such as plastics, rubbers, and lightweight metals or alloys, which are readily available to those of ordinary skill in the art. Therefore the eyewear, including the muffler tubes, can be made from similar materials. Typical plastics include polyvinyl chloride (PVC), polyethylene and polypropylene. Silicone rubbers may also be used. Suitable metals include aluminum, aluminum alloys and stainless steel.

For purposes of background and as can be understood by those skilled in the art, the noise reduction (i.e., sound attenuation) that is provided by a passive semi-insert device as described herein can be represented theoretically by the formula $P_a/P_c = A_s = (Z_e + Z_s)/Z_e$, where $P_e$ represents the sound pressure at the entrance of the ear canal, $P_a$ represents the sound pressure in the surrounding ambient air, $A_s$ represents the sound attenuation, $Z_e$ represents the acoustic impedance at the entrance of the ear canal, and $Z_s$ represents the acoustic impedance of the seal provided by the semi-insert through which sound must penetrate into the ear canal. If $Z_s$ is much larger than $Z_e$, as it should be in effective devices, the above formula can be approximated by $A_s = Z_s/Z_e$ showing that the sound (noise) attenuation is directly proportional to the acoustic impedance of the seal and inversely proportional to the acoustic impedance at the entrance of the ear canal. The principle of the herein described ear muffler tube and increased noise attenuation is realized by placing a relatively small acoustic impedance, $Z_m$, in parallel with the impedance of the ear canal, $Z_e$. When $Z_m$ is sufficiently small, the sound attenuation approaches $A_{sm} = Z_s/Z_m$ and the improvement in sound attenuation, $(A_{sm}/A_s) = (Z_e/Z_m)$. In the limit, then, the improvement is proportional to the ratio between the ear canal and the shunting impedances.

Additional detail regarding the principle and design of ear muffler tubes, in general, is provided in U.S. Pat. No. 5,824,967, herein incorporated in reference in its entirety. Fundamentally, noise attenuation is realized from a properly designed tube that provides an acoustic impedance at the open end $Z_m$ that is substantially lower than the acoustic input impedance at the entrance of the ear canal $Z_e$.

Two fundamental methods are described in the referenced '967 patent in which the acoustic impedance at the open end of the muffler tube can be made small as compared to that at the entrance of the ear canal. A first method is to make the inner cross sectional area of the muffler tube substantially larger than that of the ear canal and the muffler tube sufficiently long such that its air volume substantially exceeds that of the ear canal. The second method is to make the length of the muffler tube equal approximately to a quarter wave length of sound at a desired sound frequency. The desired effect is stronger when both of these methods are combined.

The acoustic impedance near the entrance of the ear canal has been previously measured. According to these measurements, this impedance is approximately equal on the average to the acoustic impedance of a volume of air of 1.7 cm$^3$ filled with light damping material. The lowest individual values can reach the acoustic impedance of a volume of air as large as 2.5 cm$^3$ (noting that acoustic impedance is inversely proportional to the air volume.)

A muffler tube with a cross sectional area of 1.15 cm$^2$ and a length of 4 cm has an air volume of 4.6 cm$^3$, which is almost three times as large as the average equivalent volume of the ear canal (1.7 cm$^3$) and somewhat less than twice the largest equivalent volume (about 2.5 cm$^3$). Accordingly, it should increase the sound attenuation provided by a semi-insert ear defender by a factor of about 2 to 3. This is equal in terms of the more usual logarithmic measure to about 6 to 10 dB, where sound attenuation in decibels is determined by the formula $(P_a/P_e)$ dB=20 log$(P_a/P_e)$. Therefore, a tube of 4 cm length, closed at one end, has a quarter wave resonance around 2,000 Hz. In this frequency region, the acoustic impedance at the open end of the tube is reduced well below that determined by the air volume in the tube, and the sound attenuation further enhanced the amount depending on sound absorption within the tube. In the same frequency region, the sensitivity of hearing is near its maximum and strong attenuation of ambient noise is highly beneficial.

It has also been previously determined by Applicant that lengthening the muffler tube to about 25 cm increases its air volume to about 29 cm$^3$ with a concomitant theoretical enhancement of sound attenuation provided by a semi-insert device by over 20 dB at low sound frequencies. This enhancement is further increased by a quarter wave resonance of around 350 Hz. Such a strong sound attenuation in the low frequency region would be desirable in a noise environment with strong low frequency components.

Alternatively and instead of being lengthened according to the '967 patent, the muffler tube can be made wider, such that its cross sectional area is approximately 1.5 cm$^2$ and its air volume becomes almost 3.5 times greater than the equivalent volume at the entrance of an average ear canal, this tube widening enhancing the sound attenuation nominally by about 13 dB on the average and by 10 dB in the case of the largest ear canals. The frequency of the quarter wave resonance remains unchanged, such that the muffler tube still presents to the ear canal the lowest acoustic impedance in the frequency region of 2,000 Hz.

A muffler tube that is sufficiently wide to achieve the desired noise reduction may not be accommodated comfortably in the outer ear at the entrance of the ear canal. It is often necessary to connect it to the ear canal by a narrower tube. For such a tube to interfere as little as possible with the desired acoustic effect of the muffler tube, it must be as short and wide as is compatible with the anatomy of the outer ear around the ear canal entrance. In practice, connecting tubes of 1 cm length and 0.8 cm inner diameter, equivalent approximately to a cross sectional area of 0.5 cm$^2$, have been achieved. The acoustic impedance of such a connecting tube is numerically equal to the acoustic impedance of a medium size muffler tube with a volume of air of 10 cm$^3$ at about 1,000 Hz, when the effect of the quarter wave resonance is disregarded. The resonance moves this frequency somewhat downward. The impedance is lower at lower frequencies and higher at the higher ones. This means that the connecting tube interferes little with the muffler tube below 1,000 Hz, but has a limiting effect above 1,000 Hz. Nevertheless, the acoustic impedance of such a connecting tube is lower than that at the entrance of the ear canal throughout the useful frequency range for speech communication and music, so that the connecting tube allows the attenuation of ambient noise to be enhanced in this frequency range, even though, the effect is smaller than below 1,000 Hz. Since, even without muffler tubes, semi-insert devices tend to produce acceptable noise reduction above 1,000 Hz, the decreased enhancement effect is not bothersome. It actually may be desirable under many conditions, since it leads to an approximately constant overall reduction of ambient noise throughout the practically useful range of audible sound frequencies. This prevents distortion of useful signals, such as speech and music.

In one embodiment, each muffler tube 60 together with its extension 64 measures about 13 cm in length and provides a quarter-wave resonance around 650 Hz, which further increases the ambient-noise reduction in the broad vicinity of this frequency. Decreasing or increasing the total length would shift the maximum noise reduction upward or downward in sound frequency. Decreasing or increasing the amount of sound absorbing material 88 would make the maximum frequency more or less pronounced. The muffler tube 60 has a diameter of approximately 1.5 cm, equivalent to a cross sectional area of about 1.8 $cm^2$. Increasing or decreasing the diameter would increase or decrease the amount of sound reduction, respectively. A much wider tube could become cumbersome, however, while a much narrower tube would provide a vanishing amount of noise reduction. It is estimated that a tube having a diameter equal to or smaller than about 1.2 cm, equivalent to a cross sectional area of about 1.15 $cm^2$ (that of the ear canal) would no longer usefully serve the purpose of noise reduction.

FIGS. 6-12 illustrate complete views of the eyewear embodiment of FIGS. 1-5 taken along each side thereof for more complete illustration thereof.

As previously noted, the entirety of the muffler tube 60, including the connecting tube 76 can be made from a single component or can be fabricated from multiple components. Referring to FIGS. 13(*a*)-13(*e*), various forms of connection between mating portions of a muffler tube 60 are herein depicted. For purposes of the following description, similar parts include the same reference numbers for the sake of clarity.

First and as shown in FIG. 13(*a*), a pair of mating sections 112, 116 of an extension 80 of an exemplary muffler tube 60 (partially shown) are depicted wherein one of the portions 112 is conically tapered at one end 120 and is sized to produce an interference fit when placed into engagement with the hollow end 124 of a complementary mating section 116 which is not tapered. As a result, a seamless fit can be provided with no appreciable loss in hearing protection. Preferably, an acoustic resistance element should be introduced at the formed connection. In the version shown in FIG. 13(*a*), a porous plate 125 made from sintered metal can be introduced at the juncture of the mating tubular sections 112, 114.

In the version shown in FIG. 13(*b*), a cylindrical section of sound absorbing material 88 can be introduced as an acoustic resistance element prior to inserting the tapered end 120 of the mating section 112, wherein the tapered end 120 then shifts the sound absorbing material to a desired location when assembly is complete.

In the versions shown in FIGS. 13(*c*) and 13(*d*), one end 120 of the mating section 112 is tapered as previously depicted, while the corresponding mating section 114 includes an annular shoulder 127 on the interior diameter that is sized to retain a sound absorbing ring 134 (FIG. 13(*c*)) or a sound absorbing plate 137 (FIG. 13(*d*)) between the tapered edge of the mating section 112 and the surface of the annular shoulder 127, the ring and plate being made from a suitable material, such as cloth, porous metal or plastic. In each version, a pair of concentrically mounted tubes can be used to provide an interlocking and interconnecting connection.

Another alternative embodiment shown in FIG. 13(*e*) illustrates the use of an intermediary sleeve member 146 into which the ends of a mating pair of tubular connecting sections 142, 144 of the muffler tube 60 can be individually fitted and in which foam, fibers or other acoustic resistance element(s) can be introduced. In the latter embodiment, neither tubular connecting section 142, 144 is tapered and the intermediary sleeve member 146 includes a stop 149 into which each mating end abuts.

Figure 14:
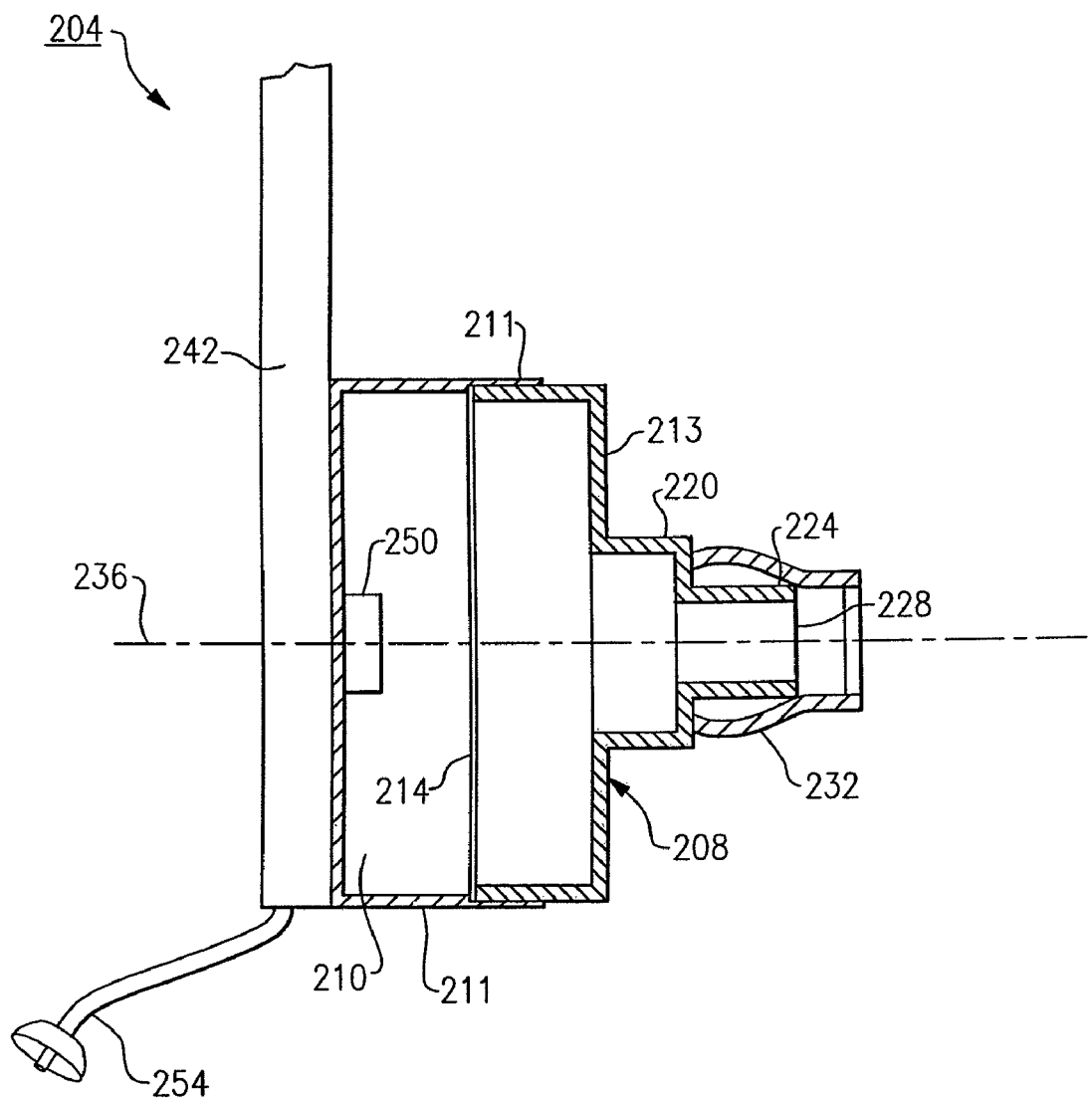
FIG. 14 is a sectioned view of a portion of a passive semi-insert hearing protection apparatus in accordance with another embodiment of the present invention that incorporates a set of eyewear.

It should be noted that the hearing protection device and integrated eyewear shown herein are merely exemplary and that other forms of passive semi-insert hearing protection devices could be provided that either integrate or include an eyewear design, as described herein. For example, another passive hearing protection device is described in U.S. Ser. No. 12/049,444, filed Mar. 18, 2008, the entire contents of which are herein incorporated by reference. A device having an exemplary design modeled on this design can be effectively produced as shown in FIG. 14.

In brief, the passive semi-insert hearing protector according to this embodiment employs a Helmholtz-type resonator. This resonator 204 can be formed by means of an enclosure 208 that is sized substantially to that of the outer ear (not shown) of the wearer, but having an interior air volume that is not smaller than about 7 cc. The enclosure 208 consists of thin walls made from a rigid or semi-rigid material, such as polyvinylchloride (PVC). The enclosure 208 can be made as a unitary component or according to this specific version, from a pair of multiple sections 211, 213 that are joined tightly together. The enclosure 208 is defined by an interior 210 having disposed therein a sound absorbing plate 214 that is pressed into contact between the fitted sections 211, 213. The porous plate 214 can consist of one or several layers of diverse materials, some of which play a sound absorbing role and some a supporting role. The enclosure 208 further includes an elongated section 220 having a substantially circular, oval, or elliptical cross section extending outwardly to a connecting tube 224, also having a circular, oval or elliptical configuration. The connecting tube 224 has an open distal end 228 extending from the interior 210 of the enclosure 208. The connecting tube 224 is designed for connection with the ear canal (not shown), wherein an exterior resilient cuff 232 is provided to enable a suitably tight seal for the resonator 204 at the entrance of the ear canal and in which the primary axis 236 of the connecting tube extends through the center of the sound absorbing plate 214 and is co-extensive therewith. Other configurations are described in the above cross referenced '444 application.

The enclosure 208 according to this embodiment is attached or formed within the frame of eyewear 242 (shown partially) that can be worn by the user. The hearing protection apparatus according to this version has an acoustic impedance at a distal end of the connecting tube 224 that is substantially smaller than the acoustic impedance at the entrance of the ear canal over a useful range of audible sound frequencies. More specifically, the porous plate 214 provides only a negligible acoustic effect at low sound frequencies, such that the resonance frequency is determined by the inertance of the connecting tube 224 with the entire volume of air in the enclosure 208. In this way, the effective acoustic compliance of the enclosure 208 is decreased and resonance frequency is increased. At higher sound frequencies, the plate 214 has the effect of reducing the effective volume of the enclosure 208 and increasing in this way the resonance frequency of the assembly. Overall, this results in broadening the frequency range of low impedance at the entrance of the tube 224. Consequently, the sound absorbing plate 214 broadens the resonance curve of the Helmholtz resonance, thus broadening the frequency band of low impedance at medium audible sound frequencies (i.e., around 1000 Hz). Alternative versions of a resonator based on the preceding principles are further described in the herein cross referenced '444 application.

Alternatively and as described in the previously cross-referenced '967 patent, either hearing protection device can further be used for sound transmission from a sound source. In this mode, a small sound-emitting transmitter can be suitably positioned within the enclosure 208 of FIG. 14, by way of example, shown herein as reference numeral 250. In addition, a small microphone 254 can also be attached to the apparatus 204.

PARTS LIST FOR FIGS. 1-14

10 hearing protection apparatus
20 safety goggles
24 eye shield
25 recess
26 frame
28 hinge members
32 hinge joint
36 front support members
40 hollow tubular section
44 distal attachment section
48 threaded fastener
52 hollow spaced holes
60 muffler tubes
64 open end
68 closed end
72 cap
76 connecting tube
80 remainder of tube
84 cuff
88 sound absorbing material
92 opening
112 mating tube section
114 mating tube section
120 tapered end
124 hollow end
125 porous plate
127 annular shoulder
134 sound absorbing ring
137 sound absorbing plate
142 tubular connecting section
144 tubular connecting section
146 intermediary sleeve member
149 stop
204 device (resonator)
208 enclosure
210 interior
211 section
213 section
214 sound absorbing plate, porous
220 elongated section
224 connecting tube
228 open distal end
232 exterior resilient cuff
236 primary axis
242 eyewear frame
250 sound-emitting transmitter
254 microphone While the present invention has been particularly shown and described with reference to the preferred mode, as illustrated in the drawings, it will be understood by one skilled in the art that various changes in detail may be effected therein without departing from the spirit and scope of the invention and according to the following claims. For example and according to yet another version, the muffler tubes can be separately clipped or otherwise attached to an existing eyewear frame.

The invention claimed is:

1. A hearing protection apparatus, said apparatus comprising: a passive semi-insert hearing protection device for reducing ambient noise to the ear of a wearer, said hearing protection device including a defined enclosure configured for communication with the ear canal of a wearer; and a set of eyewear including a eyewear frame that is integrally attached to said hearing protection device, wherein said eyewear frame incorporates the hearing protection device including said defined enclosure which is formed within said frame.

2. Apparatus according to claim 1, wherein said hearing protection device further comprises a pair of muffler tubes, each said muffler tube including an open end for coupling to the ear canal and a closed opposite end, said closed end being coupled to said frame, said tubes each having a sufficient length to provide a quarter wave sound resonance, said pair of muffler tubes forming at least a portion of said eyewear frame.

3. Apparatus according to claim 2, wherein each said muffler tube is made from at least two connecting sections.

4. Apparatus according to claim 3, wherein one of said connecting sections is tapered and is sized to fit within the interior of the other of said connecting sections.

5. Apparatus according to claim 4, including an acoustic resistance element between said tapered end and said other connecting section.

6. Apparatus according to claim 5, wherein said acoustic resistance element is one of a sound absorbing ring and a sound absorbing plate.

7. Apparatus according to claim 3, including an intermediary sleeve member into which ends of connecting tube portions are inserted.

8. Apparatus according to claim 2, wherein each of said muffler tubes is shaped to permit said frame to conform to the wearer.

9. Apparatus according to claim 8, wherein at least a portion of each said muffler tube is formed in a substantially U-shaped configuration.

10. Apparatus according to claim 9, wherein said substantially U-shaped portion is provided along a plane that is approximately orthogonal to an axis defined by a connecting tube portion of said muffler tube, said connecting tube portion being directly coupled to said ear canal.

11. Apparatus according to claim 2, wherein said muffler tubes are adjustably coupled to said connecting members.

12. Apparatus according to claim 11, wherein said connecting members are hingably attached to said frame.

13. Apparatus according to claim 12, wherein said connecting members are biasedly hinged inwardly relative to said frame.

14. Apparatus according to claim 2, wherein each of said muffler tubes is axially connected to connecting members of said eyewear frame, each of said muffler tubes and said connecting members forming individual support members of said eyewear.

15. Apparatus according to claim 2, wherein each of said muffler tubes is at least partially filled with a sound absorbing material.

16. Apparatus according to claim 2, wherein each said muffler tube is formed from a unitary section.

17. Apparatus according to claim 1, wherein said passive semi-insert hearing protection device includes an enclosure having a Helmholtz resonator disposed therein.

18. A method of manufacturing apparatus that provides both hearing and eye protection to a wearer, said method comprising the steps of:
- providing a eye protection device, said eye protection device including a set of safety goggles supported by a frame; and
- integrating a hearing protection device within said eye protection device, said integrating step including the step of forming an enclosure of said hearing protection device in said frame.

19. A method according to claim 18, wherein said hearing protection device is a passive semi-insert comprising a pair of muffler tubes, each of said muffler tubes having a closed end coupled to said frame and an open end for coupling to the ear canal of a wearer, each of said tubes having a length sufficient to provide quarter wave sound resonance.

20. A method according to claim 19, including the additional step of shaping each of said muffler tubes to conform to the head of the wearer.

21. A method according to claim 19, wherein each said muffler tube forms a side frame member of said eyewear.

22. A method according to claim 19, including the step of providing bias to each of said muffler tubes relative to the head of a wearer to provide a seal between the open end of each said muffler tube and the ear canal.

23. A method according to claim 18, including the step of assembling said muffler tubes from multiple connecting sections.

24. Apparatus for protecting the eyes and ears of a wearer, said apparatus comprising:
- a passive semi-insert hearing protection device for reducing ambient noise to the ear of a wearer, said hearing protection device comprising a pair of muffler tubes, each said muffler tube including an open end for coupling to the ear canal and a closed opposite end defining an enclosure; and
- a set of eyewear including an eyewear frame that is integrally attached to said hearing protection device, said eyewear frame including the pair of muffler tubes which are integrated, including each enclosure as a formed part of the frame, said closed end being coupled therewith and in which said muffler tubes are each defined by a sufficient length to provide a quarter wave resonance.

* * * * *